US00PP14375P29

(12) United States Plant Patent
Warren

(10) Patent No.: US PP14,375 P2
(45) Date of Patent: Dec. 16, 2003

(54) CRABAPPLE TREE NAMED 'JFS-KW5'

(50) Latin Name: *Malus transitoria*
Varietal Denomination: JFS-KW5

(75) Inventor: Keith S. Warren, Gresham, OR (US)

(73) Assignee: J. Frank & Schmidt & Co., Boring, OR (US)

( * ) Notice: Subject to any disclaimer, the term of this patent is extended or adjusted under 35 U.S.C. 154(b) by 10 days.

(21) Appl. No.: 10/123,969

(22) Filed: Apr. 16, 2002

(51) Int. Cl.[7] ..... A01H 5/00
(52) U.S. Cl. ..... Plt./173
(58) Field of Search ..... Plt./173

(56) References Cited

U.S. PATENT DOCUMENTS

PP7,147 P * 2/1990 Flemer, III ..... Plt./173
PP8,478 P * 11/1993 Fiala et al. ..... Plt./173
PP12,449 P2 * 3/2002 Krahn et al. ..... Plt./173

* cited by examiner

*Primary Examiner*—Bruce R. Campell
*Assistant Examiner*—W C Haas
(74) *Attorney, Agent, or Firm*—Klarquist Sparkman LLP

(57) ABSTRACT

A variety of crabapple which combines purple foliage color, deeply lobed ornamental vigorous growth leaves, bright reddish flowers, excellent form and foliage density, and excellent resistance to the diseases fireblight and scab.

7 Drawing Sheets

Latin name of the genus and species of the plant claimed: Malus.

Variety denomination: 'JFS-KW5'.

BACKGROUND OF THE INVENTION

In 1990, I began a program of crabapple cultivar development. In this program, I obtained select seed by both hybridizing and picking open pollinated seed off superior parent trees which are located near desirable pollinators. In 1994, I picked seed from a *Malus transitoria* 'Schmidtcutleaf' (unpatented) tree growing in the J. Frank Schmidt & Son Co. nursery arboretum in Boring, Oreg. I directed the planting of this seed in a cultivated area, and more specifically in the nursery propagation seedbeds located in Boring, Oreg. During the following summer, I noticed that among the hundreds of green leafed seedlings, three purple leafed trees were growing. I planted all the seedlings from this seed lot out into rows and began a systematic evaluation of them. Through this evaluation process, I selected my cultivar 'JFS-KW5' as a single plant and I discovered that it was superior in many ways to other seedlings in the nursery row. I first selected it because of its dark purple foliage color and apparent disease resistance. As it grew older, I discovered that it possessed attractive flowers and fruit. Over several years, I evaluated its resistance to the common crabapple diseases fireblight and apple scab. I found that my cultivar is highly resistant to both. Further observation proved that the 'JFS-KW5' variety has superior features which set it apart from other selections under observation as well as from all other existing crabapple cultivars that are in nursery production. I have directed the propagation of my cultivar by chip budding in test plots on Malus 'EMLA 111' (unpatented) understock, beginning in 1997. This asexual propagation was accomplished in Canby, Oreg. Observation of the resulting propagated plants has shown that the characteristics are firmly fixed. Trees propagated on this understock have been identical to the original parent in every manner that has been observed.

BRIEF SUMMARY OF THE INVENTION

This new cultivar possesses a unique combination of characteristics in that it combines greyed-purple summer foliage color, a deeply lobed ornamental leaf except for early leaves which tend to be entire, these early leaves appear with the flowers or shortly thereafter, bright reddish flowers, excellent form and foliage density, and excellent resistance to the diseases fireblight and scab.

BRIEF DESCRIPTION OF THE DRAWING

The accompanying illustrations show typical fruit and leaf specimens of this new crabapple variety.

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
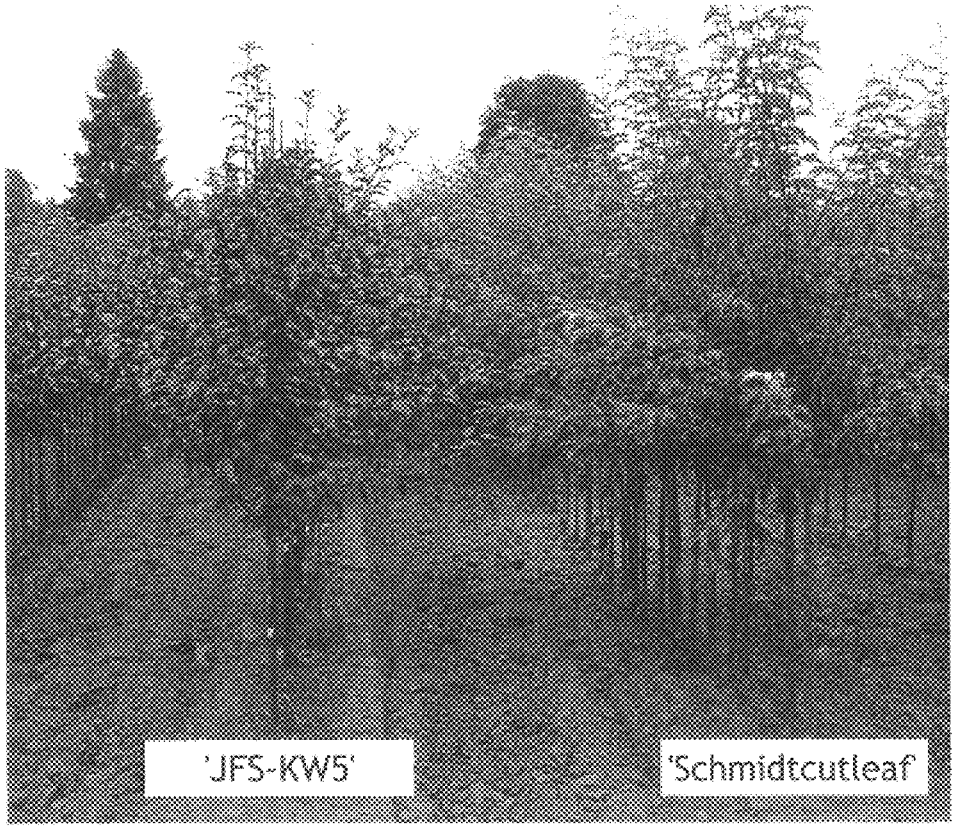
FIG. 1 shows two year old trees growing from chip bud propagation. 'JFS-KW5' is on the left; its seed parent 'Schmidtcutleaf' is on the right.
Figure 2:
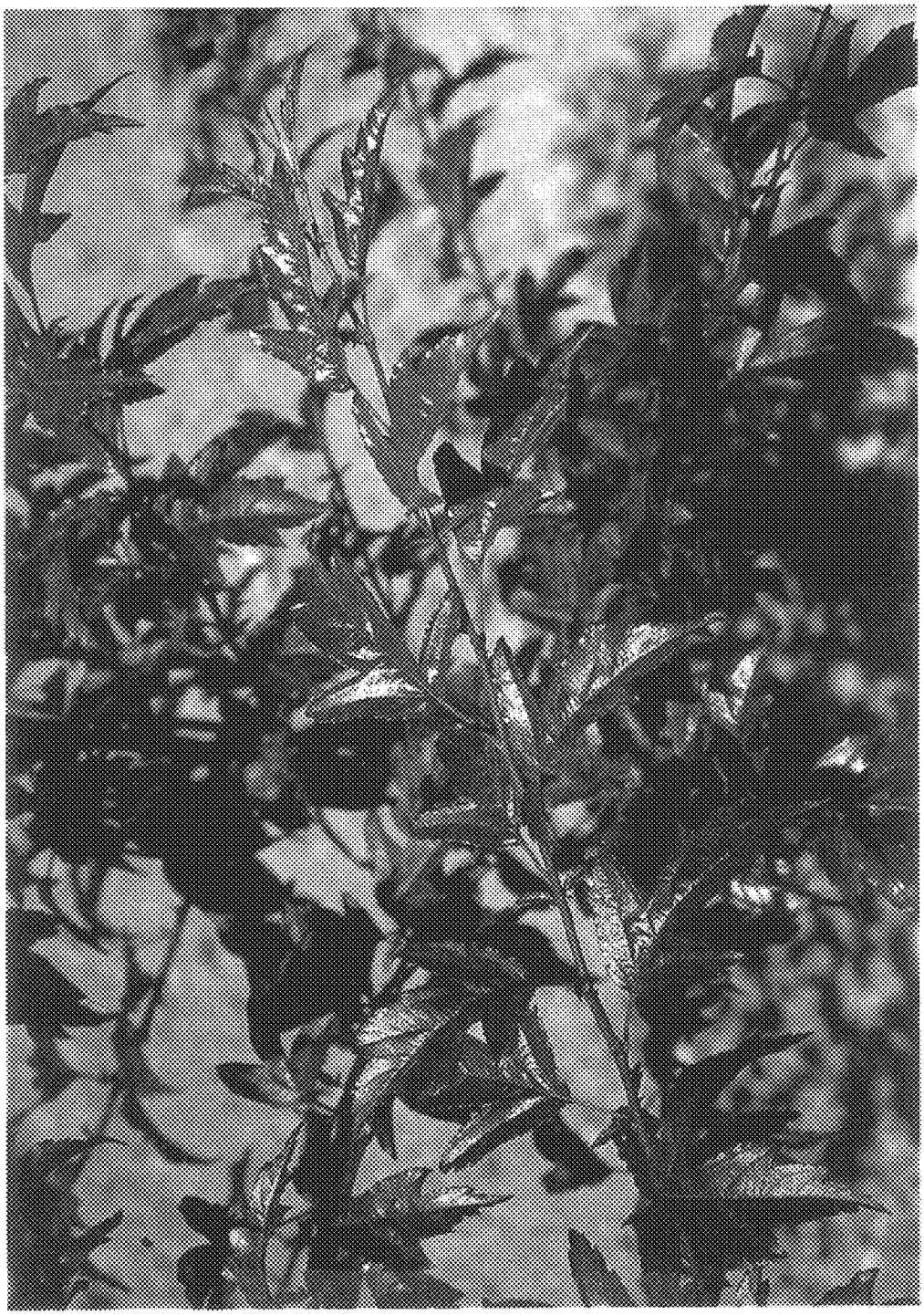
FIG. 2 shows 'JFS-KW5' leaves in summer color.
Figure 3:
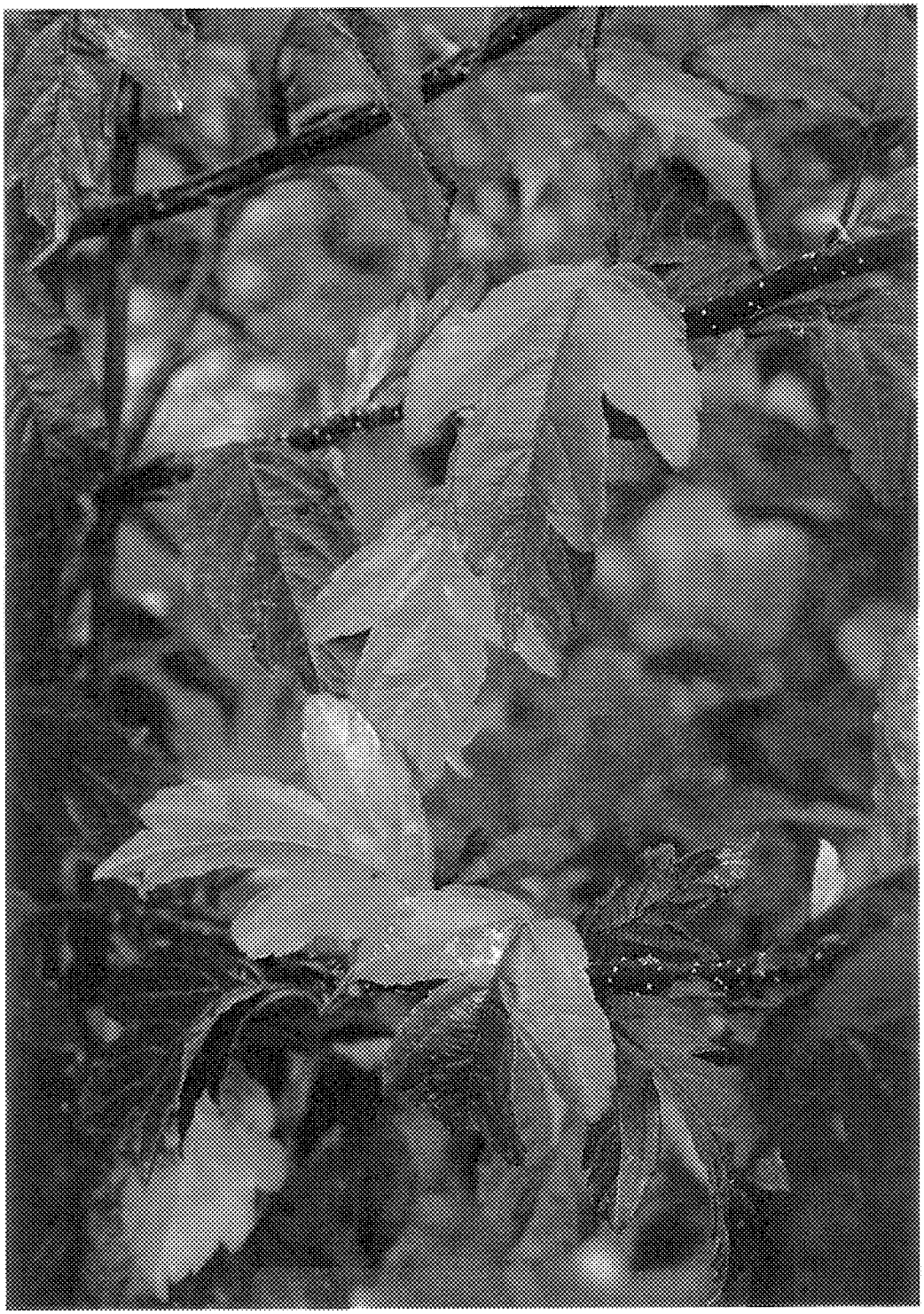
FIG. 3 shows 'JFS-KW5' leaves with some leaves in fall color.
Figure 4:
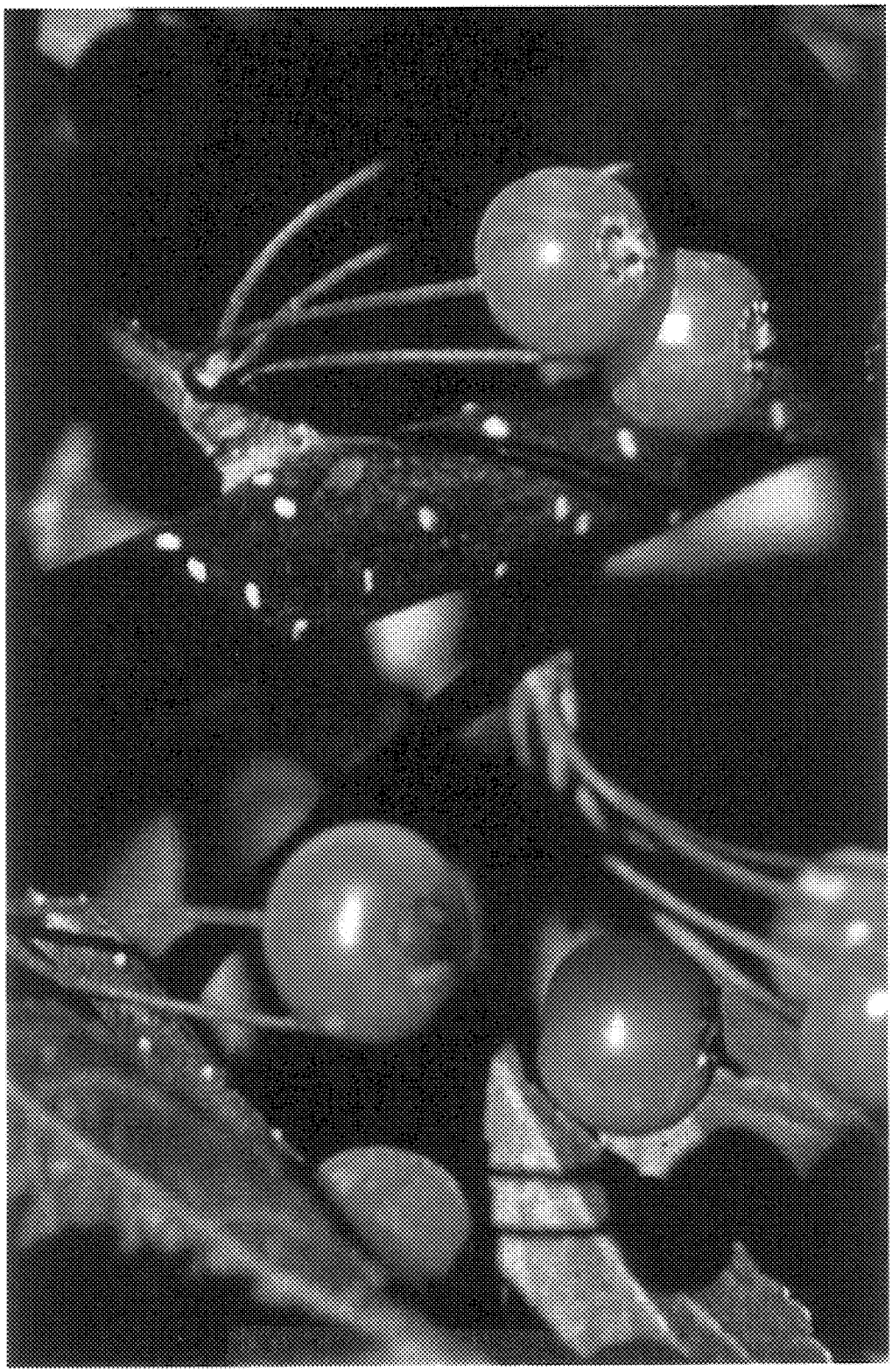
FIG. 4 shows 'JFS-KW5' fruit in early October.
Figure 5:
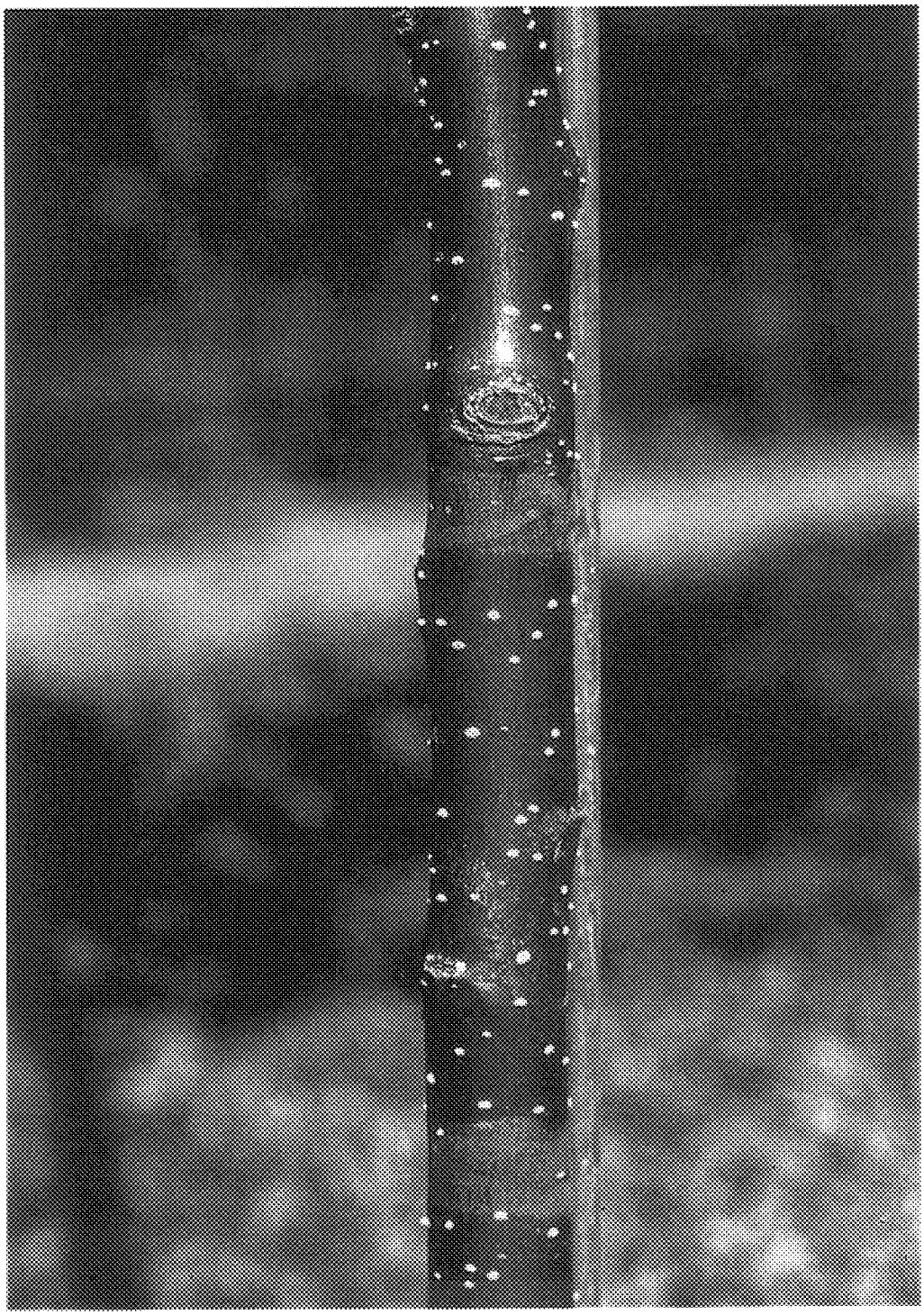
FIG. 5 shows a trunk of a two year old 'JFS-KW5' tree grown from chip budding, showing trunk color and lenticels.
Figure 6:
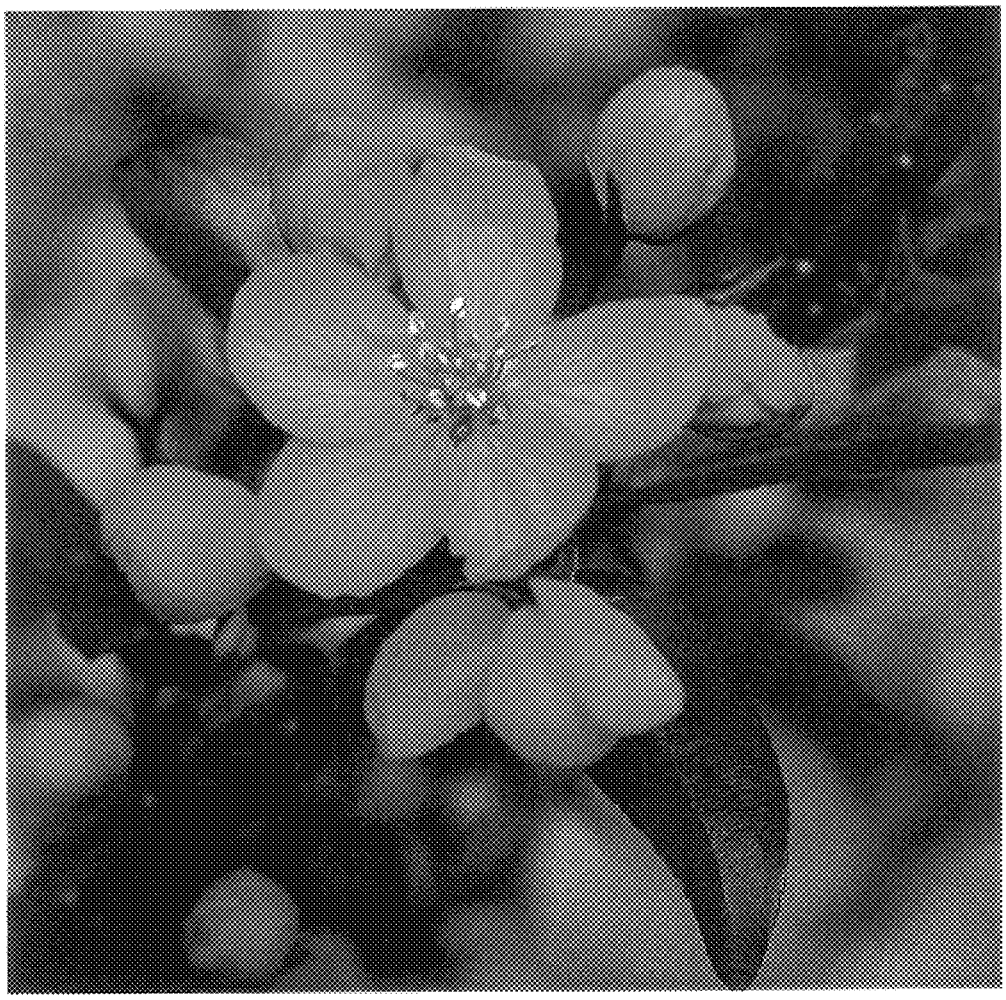
FIG. 6 shows a newly opened flower on a 'JWS-KW5' tree and buds, together with several early growth leaves.
Figure 7:
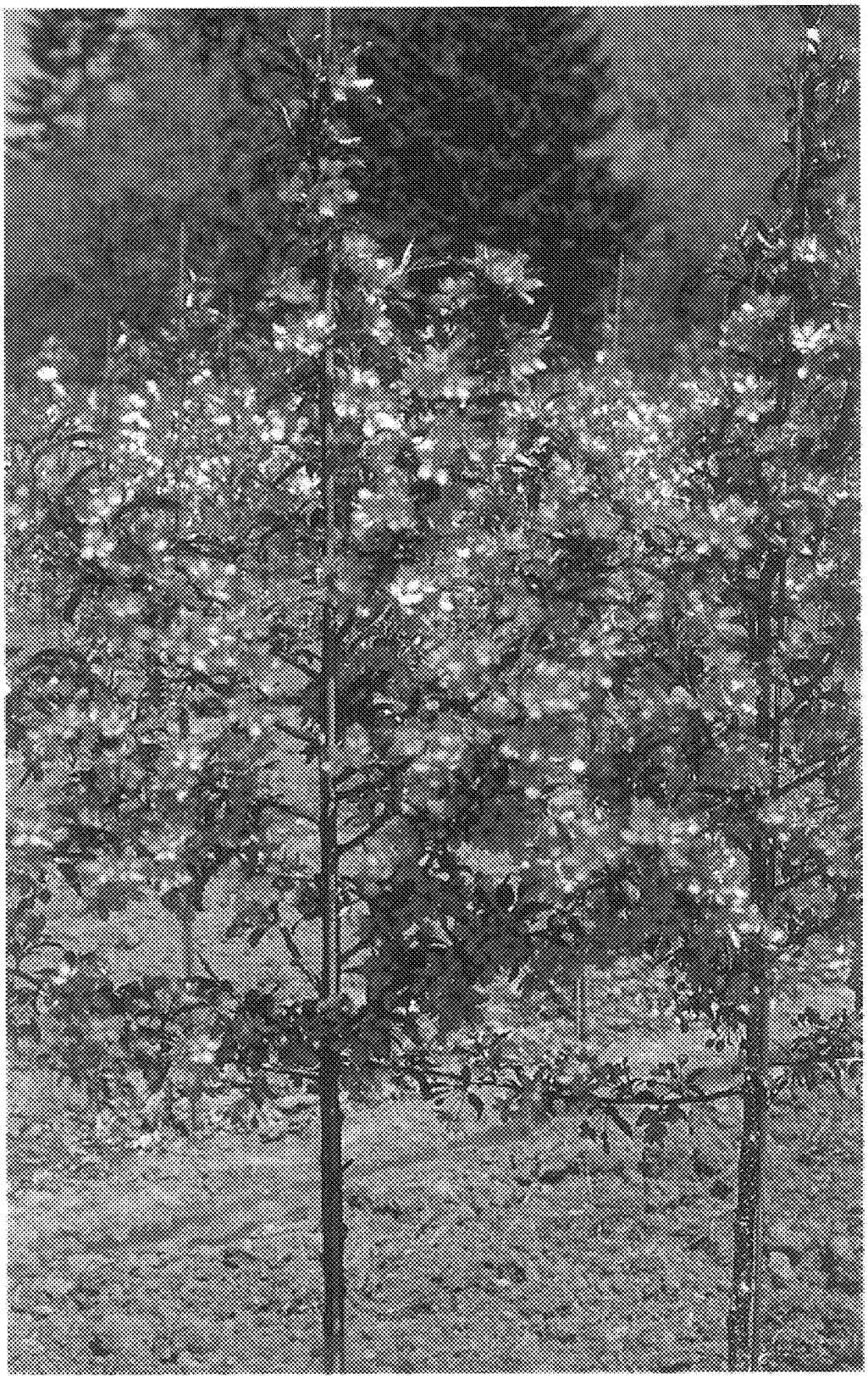
FIG. 7 shows two three-year-old 'JFW-KW5' trees, obtained by chip budding, in full flower.

The following detailed description of the 'JFS-KW5' variety is based on observations of the original tree and of two and three year old asexually reproduced progeny. The observed progeny were trees which were growing in Canby, Oreg.

Scientific name: Malus 'JFS-KW5'.
Parentage:
*Seed parent.*—*Malus transitoria* 'Schmidtcutleaf'.
*Pollen parent.*—Unknown.

'JFS-KW5' is an open pollinated seedling of *Malus transitoria* 'Schmidtcutleaf'. The pollen parent is unknown, but the features of 'JFS-KW5' lead me to believe that the pollen parent is an unknown purple leafed Malus cultivar of garden hybrid origin, several of which were growing in the vicinity of the seed parent tree. As self-pollinated *Malus transitoria* only produces green-leafed seedlings, the pollen parent is very probably a hybrid cultivar of which the dominant parentage is *Malus×purpurea*. The purple-leafed crabapple cultivars growing near the seed parent tree were hybrid cultivars which largely descended from *Malus×purpurea*. Thus, my new cultivar is probably of the hybrid origin *Malus transitoria×Malus×purpurea*.

Tree:
*Overall shape.*—Upright, spreading.
*Height.*—Original tree at about 7 years of age, about 3.6 meters high.
*Width.*—Original tree, about 2.7 meters spread.
*Caliper.*—Three year old trees, about 2.8 cm at about 20 cm above ground. This compares to about 2.4 cm for *Malus transitoria* 'Schmidtcutleaf' growing in the same area.
*Trunk.*—Strong and straight under nursery growing conditions.
*Trunk bark texture.*—Smooth with prominent lenticels.
*Trunk bark color.*—Immature bark color: Grey-purple (RHS 187A). Mature bark color: Grey-purple (RHS 187A) to brown (RHS 200A) on three year old trunks. Lenticels: Oval to elongated oval, become stretched or elongated in horizontal direction as trunk grows. They stretch until no longer apparent. Variable in size, one inch trunk has lenticels about 1 mm to 1.5 mm vertical dimension and about 2 mm horizontal dimension. Orange-white (RHS 159A) in color.
*Primary branches.*—Upright spreading growth habit; forming an upright spreading shaped crown, and developing good density of branches and foliage at a young age.
*Branch color.*—Both immature and mature branches are grey-purple (RHS 187A).
*Branch lenticels.*—Similar to trunk, horizontal in orientation, oval to elongated oval, orange-white (RHS 159A) in color.
*Dormant buds.*—Small, oval with acute tip, imbricate scales.
*Internodes.*—Moderately fast growing, average internode length is about 26 mm on a one-year old shoot.
*Hardiness.*—Not determined, observed in Hardiness Zone 8.
*Disease resistance.*—Excellent resistance to fireblight and apple scab.

Leaves: Except as otherwise noted, observations are from twenty vigorous growth leaves.
*Arrangement.*—Alternate.
*Texture.*—Slightly textured.
*Sheen.*—Glossy.
*Length.*—About 6 cm to about 8 cm.
*Width.*—About 4 cm to about 6 cm.
*Petioles.*—About 20 mm long; about 1 mm thick; grey-purple (RHS187A) in color.
*Overall shape.*—Early leaves which appear with blossoms tend to be oval to ovate and entire with finely serrate margins although some of these early leaves may have one or more lobes. Vigorous growth leaves, those which appear after the blossoms have fallen, are elongated with pointed lobes; generally five lobed, with a pair of basal lobes, a pair of distal lobes, and a tip lobe. Basal lobes are typically cut one-half of the way to the central vein. Distal lobes are typically cut approximately one-third of the way to the central vein.
*Margin.*—Finely serrate.
*Tip.*—Narrowly acute.
*Base.*—Rounded to broadly acute.
*Stipules.*—Typically two per leaf, about 6 to 10 mm long to about 2 to 3 mm wide, color similar to leaf color.
*Summer leaf color.*—Upper leaf surface: Greyed-purple (RHS 187A to 185A). Lower leaf surface: Greyed-purple (RHS 183B). Vein: Greyed-purple (RHS 185A to 187A).
*Fall leaf color.*—Red (RHS 43A) to grey-red (RHS 181A).
*Pubescence.*—Top of leaf is glabrous except for a few hairs on the veins. Lower surface of leaf is sparsely pubsecent, mostly on the veins.
*Persistence.*—Tree is deciduous.

Flowers:
*Shape.*—Symmetrical, rounded, slightly cupped.
*Size.*—Approximately 30 mm in diameter.
*Color.*—Unopened bud: About 3 to 4 mm long and 1.5–2 mm wide (based upon observations of twenty typical buds). Red in color like RHS 53B. Opened flower: Red-purple (RHS 63A) when first open. Flowers fade over time, with edges of petal becoming red-purple (RHS 64C) and center of petal becoming like red-purple (RHS 65B). Pedicel and hypanthium are red-purple (RHS 57A).
*Petals.*—Five petals per flower.
*Sepals.*—Five sepals per flower, red-purple (RHS 59A).
*Stamen.*—About fifteen to twenty stamens, length like pistil, about 9 to 12 mm long, arranged concentrically around pistil.
*Anthers.*—Yellow-orange (RHS 20B).
*Pistil.*—Compound, five branched, length about 9 mm to 12 mm. Ovary inferior, five carpels.
*Pubescence.*—Flower parts are all glabrous except sepals which are glabrous on the outside with a densely pubescent inner surface, and the pedicel which is lightly pubescent.
*Pollen.*—Yellow-orange (RHS 20B).
*Flowering date.*—In Canby, Oreg. in 2001, first bloom April 19$^{th}$, peak bloom April 25$^{th}$, last bloom May 3$^{rd}$.

Fruit: Observations are from a sampling of typical fruit.
*Size.*—Typical fruit about 8 mm to about 10 mm.
*Shape.*—Round, pome, fleshy.
*Cavity.*—None.
*Basin.*—None.
*Skin.*—Smooth.
*Lenticels.*—None observed.
*Color.*—Red (RHS 46A).

*Seeds.*—Typically 5 per fruit, ovoid with flattened sides, about 3 mm long and about 2 mm wide; smooth surface, greyed-orange (RHS 176A) in color.
*Fruit production.*—Prolific.
*Usage.*—Ornamental.

Comparison to Other Varieties

Comparison to seed parent, 'Schmidtcutleaf'

| Feature | 'JFS-KW5' | 'Schmidtcutleaf' |
|---|---|---|
| Flower color: | Red-purple 63A to 64C and 65B | White 155D |
| Leaf color, summer, | | |
| Upper surface: | Greyed-purple 187A to 185A | Green 137A |
| Lower surface: | Greyed-purple 183B | Yellow-green 146A |
| Fruit: | Red 46A | Yellow-orange 15B |

Comparison to Other Common Purple Leafed Crabapples

The most similar appearing purple leafed crabapple cultivars are Malus 'Prairifire' (unpatented) and Malus 'Purple Prince', U.S. Plant Pat. No. 8,478. My new cultivar can be easily distinguished from these others in that my cultivar has vigorous growth leaves that are typically five lobed. 'Prairifire' and 'Purple Prince' have leaves that are typically entire (no lobes) or occasionally two lobed.

I claim:

1. A new and distinct variety of crabapple tree, substantially as herein shown and described.

* * * * *